United States Patent [19]

Proudfoot

[11] 4,396,718

[45] Aug. 2, 1983

[54] FIELD TEST METHOD FOR ESTIMATION OF CONCENTRATION OF ORGANIC MATERIALS IN WATER

[75] Inventor: Clare B. Proudfoot, Munster, Ind.

[73] Assignee: The Sherwin-Williams Company, Cleveland, Ohio

[21] Appl. No.: 204,684

[22] Filed: Oct. 28, 1980

Related U.S. Application Data

[60] Division of Ser. No. 115,518, Jan. 25, 1980, Pat. No. 4,268,269, which is a continuation-in-part of Ser. No. 71,821, Sep. 4, 1979, abandoned.

[51] Int. Cl.[3] .................... G01N 31/04; G01N 31/08; G01N 33/00
[52] U.S. Cl. ........................................ 436/8; 436/98; 436/164; 422/61
[58] Field of Search .......... 252/408; 23/230 R, 230 M

[56] References Cited

U.S. PATENT DOCUMENTS 3,999,946 12/1976 Patel ..................................... 422/56
4,238,384 12/1980 Blumberg et al. ................ 23/230 R

*Primary Examiner*—Michael S. Marcus
*Attorney, Agent, or Firm*—Robert E. McDonald; James V. Tura

[57] ABSTRACT

This invention relates to use of adsorption resins and ion exchange resins to separate selected organic materials and quantify their concentration in an aqueous solution based upon comparison to a visual standard. This process can be carried out in a relatively short time period and does not require special electronic equipment. Therefore, it can be conveniently used as a field test method to determine concentration of organic materials in aqueous solutions. This invention is especially useful in quantifying the concentration of triazoles in industrial cooling water.

2 Claims, No Drawings ic materials in aqueous solutions. This invention is especially suited for determining the concentration of triazoles in water.

FIELD TEST METHOD FOR ESTIMATION OF CONCENTRATION OF ORGANIC MATERIALS IN WATER

This is a division of application Ser. No. 115,518, filed Jan. 25, 1980, now U.S. Pat. No. 4,268,269, which is a continuation-in-part of Ser. No. 071,821, filed Sept. 4, 1979 abandoned.

FIELD OF THE INVENTION

This invention relates to a convenient new analytical method for the measurement of concentration of small amounts of selected organic materials in aqueous solutions. This invention is especially suited for determining the concentration of triazoles in water.

BACKGROUND

Triazoles, especially benzotriazole and tolyltriazole, have found widespread application as corrosion inhibitors, chemical intermediates, catalysts and biocides. As corrosion inhibitors, triazoles are used in cooling water recirculating systems, antifreeze, rolling oils, cleaners, detergents, waxes, coatings, plastics and many other areas.

The level of triazole is especially critical in the cooling water usage. As industrial cooling water is lost due to evaporation, or when it is removed from the system to wash away sludge and deposits, additional fresh cooling water must be added to make up the amount lost. Since the level of triazole in the cooling water already in the system may differ from that being added along with the fresh cooling water, frequent monitoring is necessary to insure that the proper level of triazole is present in the system. In addition, once the triazole has been added to the system, the level may change due to plating out of the triazole onto the metal surfaces or possible reaction of triazole with contaminants in the aqueous system. Since it is important to maintain the concentration of triazole in the preferred range for corrosion inhibition, e.g. 1 to 10 parts per million, the cooling water must be frequently monitored to maintain the proper level of triazole. In a number of industries, this monitoring may be required on a daily basis.

Due to the importance of accurate measuring of the triazole concentration, several analytical methods for measuring this level have been proposed in the prior art. These methods include gas chromatography, spectrophotometry, liquid chromatography, potentiometry and various gravometric determinations. Discussions of these methods are presented in several literature sources including: Fagel, J. E., Jr., Ewing, G. W., Journal of the American Chemical Society, 73, (1951) 4360; Harrison, S., and Woodroffe, G. L., Analyst, 90, (1965) 44; Keil, R., Z. Anal. Chem., 71, (1971) 257; American National Standards Institute, ANSI PH 4, 204-1972; and Sherwin-Williams Company, Technical Bulletin 550, Revision B and other technical journals and publications.

All of the methods outlined in the prior art have several drawbacks. They are typically time consuming and they require skilled operators and relatively expensive analytical equipment which would not be conveniently located at the site of the cooling water. This invention overcomes the limitations of the prior art methods by providing an inexpensive and relatively rapid means of determining triazole concentration based upon a simple visual comparison. This invention provides a method which is convenient to use in the field at the site of the cooling water and does not require specially trained personnel to perform the test. This invention is capable of determining the level of triazole in concentrations of one part per million or less by a simple procedure which involves first a separation of the triazole from the aqueous solution and then a quantification based on the formation of a colored triazole complex.

SUMMARY

It is an object of this invention to provide a convenient, inexpensive method for determining the concentration of organic materials, especially triazoles, in an aqueous solution based upon comparison to a visual standard. Another object of this invention is to provide a field test kit for convenient on site determination of the concentration of triazole in an aqueous sample. Another object of this invention is to provide a method of determination of triazole concentration based on the formation of a colored triazole-metal ion complex. Still another object of this invention is to provide a method of determining triazole concentration in an aqueous solution which minimizes the effects of contaminants in the aqueous solution. A more limited object of this invention is to provide a method for determining the concentration of triazole in cooling water. These and other objects of this invention will be apparent from the following description.

According to this invention, triazoles such as tolyltriazole and benzotriazole can be determined at concentrations of one part per million or less by a simple procedure. The preferred process for practicing this invention involves a separation step and a quantification step. The separation is necessary because the aqueous solutions which contain triazole frequently have other components such as dissolved gases, mineral salts, scale inhibitors and so forth which could interfere with the quantification step. For the purposes of this invention, a practical adsorbing medium for separating the triazole is one which would preferentially and quantitatively adsorb the triazole from the aqueous solution, but which would allow essentially complete recovery of the triazole upon desorption. As used herein, preferentially adsorbed means essentially all of the triazole is adsorbed while essentially none of the interfering impurities are adsorbed. Some of the solid type sorbents such as carbons or powdered copper metal are very effective as sorbents but they do not permit efficient, convenient recovery of the sorbed organic material. Therefore, the preferred method of practicing this invention involves use of a non-ionic macroreticular resin as the sorbing material for the purification step. There are a number of these resins commercially available and there are a number of prior art references which show that these materials are effective in separating organic materials from aqueous solutions. See, for example, G. A. Junk et al, Journal of Chromatography, 99 (1974) 745–762, or Tateda and Fritz, Journal of Chromatography, 152 (1978) 329–340 as well as many other articles and publications within the chromatographic literature. None of the references, however, suggest the use of the macroreticular resin in combination with a second step involving an ion exchange resin to produce a quantification of the concentration of an organic material by comparison to a visual standard as this invention teaches. Especially suited for use in this invention as the adsorbing medium is Amberlite XAD-4 (a low polarity, non-ionic macroreticular styrene-divinylbenzene copolymer manufactured by the Rohm and Haas Co.) although other similar materials well known in the art could also be used.

Using standard techniques well known within the chromatographic sciences, the adsorbing medium can be conveniently slurried and added to a glass chromatographic column to produce an effective depth of the adsorbing medium which can then be washed with water. Typically, a depth of about 2–3 centimeters is effective for the concentrations of triazole present in cooling water. The triazole to be isolated can then be sorbed onto the macroreticular resin by simply passing the triazole containing aqueous solution through the chromatographic column.

The preferred method for preparing the Amberlite XAD-4 columns is to grind a commercial sample of Amberlite XAD-4 to about 100 to 200 mesh, remove fine materials by decanting alternately with acetone and water, and adding the resin as a water slurry to the glass chromatographic column.

Once the triazole has been separated from the aqueous solution by sorption onto the macroreticular resin, the triazole can be desorbed by passing a suitable eluting solvent through the macroreticular resin. Suitable eluting solvents are those which will recover essentially all of the adsorbed triazole and they typically include ketones, ethers, alcohols, esters and other materials known in the art. The preferred solvent for use in this invention is acetone, although other solvents are also effective. It is preferred to minimize the amount of the eluting solvent used because excessive amounts of solvent may cause severe bubbling in the ion-exchange resin during the quantification step which interferes with the flow of the solution. Excessive amounts of solvent may also prevent quantitative retention of the triazole by the ion-exchange resin. Therefore, for the most accurate results, effective amounts of the eluting solvent would be less than about 3 milliliters total and a preferred amount would be between about 1.5 to 2.5 milliliters total.

The eluate which contains the previously adsorbed triazole and the eluting solvent is essentially free from impurities which would interfere with the quantification aspects of this invention. Since many organic materials do not lend themselves to colorimetric determinations in their original state, this invention relies on making a colored organic-metal ion complex for the quantification step. The colored complex could then be compared to a visual standard which has been calibrated on a concentration scale showing intensity and amount of color as a function of concentration.

The preferred method for preparing the colored complex within the teaching of this invention is to pass the eluate through an ion exchange resin which has been converted to metal ion form. The most suitable ion exchange resins for use in this invention are the acidic cationic exchange resins. These resins can be readily converted to the metal ion form by washing the resin several times with a solution containing a salt of the metal as is well known in the art. In the preferred method for practicing this invention an acidic cationic ion exchange resin such as Dowex 50W-X2 (cation exchange resin, 100–200 mesh in the hydrogen form from Bio-Rad Laboratories) is slurried and added to a glass chromatographic column to produce an effective depth (normally about 2–3 centimeters) of the ion exchange resin. The resin is then washed several times with distilled water and can then be immediately converted to the metal ion form by washing with a solution of a metal salt or, preferably, the end of the column can be capped and the aqueous slurry of the resin stored under several milliliters (typically about 5 mls.) of the aqueous salt solution. In the later instance, the metal salt solution need not be allowed to flow through the ion exchange resin until the eluate from the purification step is added to the column. In either case, the solution of the metal salt could have a concentration of up to about 1.0 molar or higher, but it is preferred to use a lesser concentration (e.g. from 0.05 to 0.2 molar) in order to prevent crystallization. The preferred metal ion is cupric (obtained by washing the resin with a cupric sulfate solution). Ions from other metals such as cobalt are also effective in producing colored complexes with triazoles, but concentration measurements using these other ions do not always provide the reproducibility obtainable with cupric ion and therefore they are not preferred in the practice of this invention.

Once the triazole containing eluate from the purification step is passed through the metal ion cationic exchange resin, the triazole is strongly bound to the surface of the resin as the colored metal ion-triazole complex. The excess metal ions can then be eluted from the column by washing with an aqueous inorganic salt solution to leave a narrow colored band of the triazole-metal ion complex strongly adhered to the surface. Especially preferred as aqueous inorganic salts are the aqueous solutions of the alkali metal chlorides, in particular potassium chloride or sodium chloride. The concentration of the aqueous inorganic salt does not appear to be critical, however, for handling efficiency, it is generally preferred that the concentrations range from about 100 grams per liter up to saturated solutions. Typically less than about 5 milliliters of an aqueous inorganic salt within that concentration range will be necessary to elute the unreacted metal ion from a 3 centimeter depth of the cation exchange resin. The amount of aqueous inorganic salt solution needed can be easily determined visually because as it is added it washes away the colored, unreacted ions to expose the uncolored resin.

By visual comparison of the size and color of the band with a visual standard showing bands produced by known amounts of triazole, it is possible to estimate the concentration of an unknown to within one part per million in the range of about 1 to 5 parts per million. Higher or lower concentration of triazole could be accommodated within the process by varying the amount of sample used.

Although other methods of preparing visual standards such as photographs or printed cards are not excluded, the preferred method of preparing the visual standards involves preparing the actual narrow colored bands on the ion exchange resins by passing a known concentration of triazole through each individual chromatographic column. A series of these columns can be prepared showing incremental changes in the total concentration of triazole. These columns can then be capped and stored until needed. When the unknown sample of triazole is passed through a column and adsorbed onto a similar resin, the depth and color of that band can then be compared to the series of standards of known concentration and the concentration of the unknown can be rapidly and accurately estimated.

A convenient portable kit can be prepared and easily carried on site for determination of triazole concentration in cooling water. The kit could contain several chromatographic columns already containing the macroreticular resin, several columns containing the ion exchange resin along with the necessary solvents and the visual standards. The process outlined in this invention is easily learned and can be executed on site in a time period of about 20 to 30 minutes.

Although this process is especially suited for the determination of triazole content in an aqueous solution, any organic material which could be preferentially adsorbed on a macroreticular resin and which would form a strongly adhering visible complex upon contact with an ion exchange resin in the metal ion form could be used within the scope of this invention. Initial indications are that the process may be quite effective in determination of concentration of carboxybenzotriazole and its esters, benzimidazole, and other materials as well as benzotriazole and tolyltriazole.

DESCRIPTION OF THE PREFERRED EMBODIMENTS

The following examples have been selected to illustrate specific embodiments and practices of advantage to a more complete understanding of the invention. In all cases, unless otherwise specified in the examples, all reagents are of reagent quality, water is distilled or deionized and all chromatographic columns are 0.7 cm ID × 10 cm length.

EXAMPLE I

Preparation of Macroreticular Resin

A quantity of Amberlite XAD-4 Resin from Rohm and Haas Company, was ground to 100 to 200 mesh, dried and washed several times by decantation with acetone until the finely suspended material was removed. The acetone was then drained off and the resin again washed several times by decantation with methanol. A polypropylene filling funnel is attached to one of the chromatographic columns and sufficient amounts of the Amberlite XAD-4 resin slurry are added to establish a bed of approximately two centimeters in depth. The methanol is allowed to drain out and the resin is washed with several milliliters of water. Additional resin which is not used immediately, can be stored in a dropping bottle under methanol.

EXAMPLE I-A

Alternative Preparation of Macroreticular Resin

The procedure of Example I is followed except the resin is not dried after grinding and it is decanted by water instead of methanol. This resin can be added to the columns as a water slurry immediately or stored as is for later use. A column prepared in this manner is at least equally effective with that prepared in Example I.

EXAMPLE II

Preparation of Metal Ion Form of Ion Exchange Resin

A quantity of Dowex 50W-X2 cation exchange resin, 100 to 200 mesh, in the hydrogen form, was washed several times with distilled water and with a one molar solution of cupric sulfate, after which it was again washed several times with water. The converted resin can be stored as a slurry in a dropping bottle or it can be immediately introduced into a chromatographic column in sufficient quantities to provide a bed of approximately two centimeters depth. When these columns are used during the quantification step, it is important to avoid disruption of the resin bed after the sample has been introduced and it is helpful to maintain at least one or two centimeters of liquid above the resin surface at all times.

EXAMPLE II-A

Alternative Preparation of Metal Ion Form of Ion Exchange Resin

A quantity of Dowex 50W-X2 was washed several times with distilled water then added as a water slurry to a chromatographic column to a depth of about 3 cm. The outlet was capped and 5 milliliters of 0.1 molar aqueous cupric sulfate was introduced into the top of the column. A glass wool plug was then inserted to a level just above the resin surface. When a column prepared in this manner is used to measure the triazole concentration it is often convenient to drain the eluate from the macroreticular resin directly onto the cupric sulfate solution above the resin surface and then allow all the liquid to drain down to the level of the glass wool. The resin can then be rinsed with about 5 milliliters of water followed by about 5 milliliters of aqueous potassium chloride (e.g. 200 g. potassium chloride per liter of water) to elute the unreacted ions. The exposed color band can be compared to a visual standard to determine concentration.

EXAMPLE III

Preparation of Visual Standards

A triazole standard solution is prepared by accurately weighing out 0.100 gram of the selected triazole (e.g. benzotriazole or tolyltriazole) which is then dissolved in 1000 mls of water. A series of five chromatographic columns containing the metal ion form of the ion exchange resin are prepared as shown in Example II. Using a calibrated syringe, from 1 to 5 mls of the triazole standard solution in one ml increments is added to each of the individual chromatographic columns so that one column receives one ml, the next column 2 mls and so on. Each column is then rinsed with ten milliliters of water followed by two to three milliliters of a solution of potassium chloride (200 grams potassium chloride per liter of water) to rinse the remaining unreacted metal ions out of the column. Each of the five chromatographic columns so prepared shows an incremental increase in the size and color of the band which is determined by the total amount of triazole in the solution. By comparing an unknown sample to the size and shape of the bands in the standards, the quantity of triazole in the unknown solution can be readily determined.

In order to determine how accurate this visual test would be in comparison with the standard, more time consuming analytical procedures, samples of industrial cooling water were obtained from eight different industrial sites and measured both by conventional analytical techniques (usually ultraviolet spectrophotometry) and the new technique described in this invention. The eight samples are described in Examples IV through XI and a summary of the comparative results is given in Table I, below.

EXAMPLE IV 1 milliliter of industrial cooling treatment for diesel systems containing 112.3 ppm tolyltriazole in 50% sodium zeolite softened tap water and 50% ethylene glycol (industrial grade) is added to a column of macroreticular resin prepared as described in Example I.

The sample is allowed to drain out completely and the effluent is discarded.

A 100 milliliter vial is placed under the column outlet and a dropper full of acetone is introduced in the top of the column and allowed to permeate the bed. The acetone addition is repeated three more times, allowing about one minute between each addition. The eluate is collected and then diluted with approximately two volumes of water.

The diluted eluate from the separation step is added to the chromatographic column containing the metal ion form of the ion exchange resin prepared as described in Example II. The eluate is allowed to flow through the column and when nearly through is followed with 10 mils of water. When the water rinse is nearly through the column two to three milliliters of a potassium chloride solution (200 grams potassium chloride per liter) is added to the column to remove the unreacted metal ions. After this has nearly passed through, the column outlet is capped and the color intensity and size of the remaining green band is compared with the standards prepared as described in Example III. This comparison indicated a tolyltriazole level of 100 ppm in the sample.

EXAMPLE V 100 mls of an industrial cooling system designed for open recirculating cooling water which contains 2.50 ppm of benzotriazole in tap water is passed through the macroreticular resin and the ion exchange resin as described in Example IV. Comparison to the visual standards based upon the size of the green band obtained in the technique described in this invention indicated a benzotriazole content of 2.0 parts per million.

EXAMPLE VI 100 mls of a solution of cooling water containing 3.75 ppm of benzotriazole in tap water is passed through a column of macroreticular resin and a column of ion exchange resin as described in Example IV. Comparison of the size and intensity of the colored band to the visual standards indicated a triazole level of 3.5 parts per million.

EXAMPLE VII 100 milliliters of an industrial cooling water system containing 2 ppm tolyltriazole in simulated cooling tower water is passed through the macroreticular resin and the ion exchange resin as described in Example IV. Comparison of the size and intensity of the green band obtained in the industrial sample to the prepared standards indicated a triazole level of 2 parts per million.

EXAMPLE VIII 100 milliliters of a cooling water solution containing five parts per million each of Dequest 2010, Cyanamer P-70, Sodium Molybdate, sodium hydroxide equivalent to 30 ppm, zinc chloride at 2 ppm and benzotriazole at 1 ppm was passed through the chromatographic columns containing the macroreticular resin and the ion exchange resin as described in Example IV. Comparison of the green band obtained with the standard materials prepared in Example III indicated a triazole level of 1 ppm.

EXAMPLE IX

A water treatment concentrate containing an unspecified polymer, chromates, phosphonates and tolyltriazole was obtained from an industrial source. The tolyltriazole content was determined by ultraviolet spectrophotometry to be 7.4 grams per liter. In order to bring this high concentration within the range covered by the standards, 4 ml of the concentrate was diluted with water to give a final volume of 10,000 mls. 100 milliliters of this dilute solution was tested as described in Example IV. Comparison of the green band obtained for this sample with bands in the visual standards, indicated a triazole level of 3 ppm in the dilution which was equivalent to 7.5 grams per liter in the concentrate.

EXAMPLE X

A cooling water feed solution containing 110 parts per million of hardness and 3 parts per million of added tolyltriazole was obtained from a corrosion research laboratory. 100 milliliters of this solution was tested as described in Example IV. Comparison with the visual standards indicated a level of 3 parts per million of triazole in the solution.

EXAMPLE XI

A cooling water feed solution containing 220 parts per million hardness and 2 parts per million of added tolyltriazole was obtained from a corrosion research laboratory. 100 milliliters of this solution was tested as described in Example IV. Comparison of the green band obtained to the visual standards indicated a level of triazole of 2 parts per million.

These examples are summarized below in Table I.

TABLE I

Comparison of Levels of Triazole Found

| Example No. | Triazole Present by Analytical Determination[a] | Triazole Present by Method of This Invention |
|---|---|---|
| IV | 112.0 ppm | 100 ppm |
| V | 2.5 ppm | 2 ppm |
| VI | 3.75 ppm | 3.5 ppm |
| VII | 2 ppm | 2 ppm |
| VIII | 1 ppm | 1 ppm |
| IX | 7.4 g/l | 7.5 g/l |
| X | 3 ppm | 3 ppm |
| XI | 2 ppm | 2 ppm |

[a] Analytical determinations of triazole present for Examples IV through IX were made by ultraviolet spectrophotometry. For Examples X and XI, accurately weighed samples of triazole were added to those solutions to produce a known concentration.

As can be seen from Examples IV through XI, which are summarized in Table I, this invention provides a rapid and accurate means of determining the level of triazole present in cooling water despite the presence of impurities, hardness, salts or other organic chemicals.

The foregoing examples, while illustrative, are not exhaustive and while this invention has been described by a number of specific embodiments, it is obvious that other variations and modifications may be made without departing from the spirit and scope of the invention set forth in the appended claims.

The invention claimed is:

1. A visual standard useful in the quantitative identification of concentrations of triazoles in aqueous solutions by visual determination, said standard comprising a series of colored metal ion triazole complexes, each element in the series having a concentration incrementally varied from the others, wherein each element of the series is prepared by a process which comprises:
   (a) passing an aqueous solution having a known concentration of triazole through an ion exchange resin, wherein said ion exchange resin is in metal ion form and wherein said metal ions are reactive towards said triazole; and (b) eluting excess metal ions from said ion exchange resin by addition of an effective amount of an aqueous inorganic salt to expose the adsorbed metal ion triazole colored product.

2. A test kit useful for the quantitative identification of concentrations of triazoles in aqueous solutions said test kit comprising:

1. a plurality of columns containing a non-ionic macroreticular resin; and
2. a plurality of columns containing an acidic cationic ion exchange resin in metal ion form; and
3. containers containing solvents capable of eluting triazole which is adsorbed onto the macroreticular resin; and
4. a container containing an aqueous inorganic salt solution capable of washing excess metal ion from the acidic cationic ion exchange resin; and
5. a visual standard useful in the quantitative determination of concentrations of triazoles by visual comparison, said standard comprising a series of colored metal ion triazole complexes, each element in the series having a concentration incrementally varied from the others, wherein each element of the series is prepared by a process which comprises:

(a) passing an aqueous solution having a known concentration or triazole through an ion exchange resin, wherein said ion exchange resin is in metal ion form and wherein said metal ions are reactive towards said triazole; and (b) eluting excess metal ions from said ion exchange resin by addition of an effective amount of an aqueous inorganic salt to expose the adsorbed metal ion triazole colored product.

* * * * *